US006759395B2

(12) United States Patent
Rao et al.

(10) Patent No.: US 6,759,395 B2
(45) Date of Patent: Jul. 6, 2004

(54) SOFT-GELATIN CAPSULE COMPRISING S-ADENOSYLMETHIONINE AND A METHOD FOR PRODUCING THE SAME

(75) Inventors: Canakapalli Bhaktavatsala Rao, Tamil Nadu (IN); Prasanta Kumar Chakrabarti, Tamil Nadu (IN); Hema Ravishankar, Tamil Nadu (IN)

(73) Assignee: Orchid Chemicals & Pharmaceuticals, Ltd., Tamil Nadu (IN)

( * ) Notice: Subject to any disclaimer, the term of this patent is extended or adjusted under 35 U.S.C. 154(b) by 0 days.

(21) Appl. No.: 10/020,184

(22) Filed: Dec. 18, 2001

(65) Prior Publication Data

US 2002/0164369 A1 Nov. 7, 2002

Related U.S. Application Data

(60) Provisional application No. 60/255,901, filed on Dec. 18, 2000.

(51) Int. Cl.[7] .................. A01N 43/04; A61K 31/70; A61K 9/64; A61K 9/52; A61K 9/84
(52) U.S. Cl. ............... 514/45; 514/46; 536/26.13; 536/27.3; 536/27.31; 424/456; 424/457; 424/458; 424/463
(58) Field of Search ............... 514/45, 46; 536/26.13; 536/27.31; 424/456, 457, 458, 463

(56) References Cited

U.S. PATENT DOCUMENTS 3,893,999 A 7/1975 Fiecchi
3,954,726 A * 5/1976 Fiecchi ............... 536/27.31
4,057,686 A 11/1977 Fiecchi
4,109,079 A 8/1978 Kawahara et al.
4,242,505 A 12/1980 Kawahara et al.
4,287,221 A 9/1981 Tonedachi et al.
4,369,177 A 1/1983 Kozaki et al.
4,764,603 A * 8/1988 Zappia et al. ............ 536/27.3
4,816,259 A * 3/1989 Matthews et al. .......... 424/463
5,073,546 A 12/1991 Zappia et al.
5,114,931 A 5/1992 Gennari
5,128,249 A 7/1992 Gennari
5,543,417 A * 8/1996 Waldstreicher ............ 514/284
5,595,758 A * 1/1997 Adusumilli et al. ........ 424/456
6,093,703 A 7/2000 La Greca
6,117,849 A * 9/2000 Zimmermann et al. ....... 514/45

FOREIGN PATENT DOCUMENTS

EP 0136464 A2 4/1985
EP 0620004 A1 10/1994

* cited by examiner

Primary Examiner—James O. Wilson
Assistant Examiner—Traviss C. McIntosh, III
(74) Attorney, Agent, or Firm—Burns, Doane, Swecker & Mathis, L.L.P.

(57) ABSTRACT

The invention provides a novel soft gelatin capsule comprising a fill material consisting essentially of S-adenosylmethionine (SAMe) salt disposed within an enteric coated soft gelatin film.

30 Claims, No Drawings ically stable and durable dosage form that will promote# SOFT-GELATIN CAPSULE COMPRISING S-ADENOSYLMETHIONINE AND A METHOD FOR PRODUCING THE SAME This application claims priority under 35 U.S.C. § 119 to U.S. Provisional Application No. 60/255,901 entitled A NOVEL SOFT-GELATIN CAPSULE COMPRISING S-ADENOSYLMETHIONINE AND A METHOD FOR PRODUCING THE SAME and filed on Dec. 18, 2000, the entire content of which is hereby incorporated by reference.

FIELD OF THE INVENTION

The invention relates to a soft gelatin capsule comprising S-adenosylmethionine (SAMe) and a method for producing such a capsule.

BACKGROUND AND PRIOR ART REFERENCES OF THE INVENTION

S-adenosylmethionine participates in a great number of metabolic processes of fundamental importance for human organism, and consequently its deficiency lies at the basis of many organic malfunctions.

S-adenosylmethionine is a natural molecule synthesized from the amino acid methionine in the presence of magnesium and adenosine triphosphate (ATP). The SAMe molecule is a carrier of methyl groups and provides a sulfur molecule as well. The liver is a site of methylation and sulfation reactions necessary for detoxification, and can use SAMe to assist in these processes. SAMe is also a cofactor in several metabolic reactions. By donating its methyl group, SAMe is converted to adenosylhomocysteine which, in turn, is rapidly hydrolysed to adenosine and homocysteine and eventually to the amino acid, cysteine.

S-adenosylmethionine is necessary for the production of Glutathione, the primary antioxidant found in the liver. SAMe has also been found effective in the treatment of Cholestasis. SAMe is also used in the treatment of fibromyalgia, osteoarthritis and depression.

SAMe is a highly temperature sensitive and moisture sensitive material. Therefore, several workers have attempted to provide stable salts of SAMe which can be used in drug formulations (e.g. U.S. Pat. Nos. 5,114,931 and 4,309,177 which are incorporated herein by reference). Two basic classes of derivatives have emerged, such as 1–4 butane sulphonates and disulphate tosylates. Examples of such salts can be found in U.S. Pat. No. 3,893,999 (SAMe tripara toulene sulphonate) and U.S. Pat. No. 4,057,686. These salts can be prepared by conventional methods such as fermentation or the synthetic route. These salts also need to be stored generally at 8 to 15° C. in a cool dry place.

The salts of U.S. Pat. No. 3,893,999 are said to be sufficiently stable at 25° C. and U.S. Pat. Nos. 3,954,726 and 4,057,686 provide SAMe salts claimed to be stable at 45° C. Thus, most SAMe salts are hygroscopic and quickly degrade on exposure to moisture and heat. Pharmacokinetic studies conducted in respect of SAMe suggest that the drug is mainly absorbed in the intestinal tract, specifically, the duodenum. Currently, SAMe is available in the market in the tablet form. The absorption time of this drug in solid dosage form is relatively long and erratic for at least two reasons: one—the drug is introduced into the body as a solid: it therefore must dissolve before it can be absorbed by the body; second reason is the acidic environment of the stomach. SAMe salts are influenced by the highly acidic environment of the stomach and often, the active ingredient does not get absorbed in the intestine as intended or desired by the manufacturer.

There is thus, a pronounced need in the art to provide a physically stable and durable dosage form that will promote timely absorption of the drug.

The prior art is replete with examples of drugs wherein one particular dosage form has been found unsuitable and alternative forms have been provided. Therefore, it would be ideal to provide an alternative dosage form of SAMe, which can be easily absorbed by the human body.

Extended release delivery systems capable of releasing a drug after a predetermined time at target site have been studied to address the problematic areas in sustained release preparations. It is found that encapsulation of the medicinal agent may be a good option, considering consumer acceptability, reduced scope for tampering and capacity to release the drug after a predetermined lag time. This art of encapsulation has gained importance over the years as an alternative to tablets. The capsule form also presents several significant advantages over tablets, like they are tasteless, odorless, easy to swallow, etc.

As said earlier, SAMe being hygroscopic, is susceptible to degradation on exposure to heat and moisture. It is, however, more stable in a lipophilic environment. It should theoretically be possible to formulate and provide SAMe in an encapsulated form for good bioavailability, using methods known in the art.

Several patents providing various 'stable' salts of SAMe, such as U.S. Pat. Nos. 4,109,079; 4,242,505; 4,764,603; 5,073,546; 5,128,249; 5,238,741 and 6,093,703, make references and even suggest the preparation of pharmaceutical formulations using these salts as active ingredients. U.S. Pat. No. 5,128,249 provides sulpho salts suitable for oral use and describes in Example 13, the ingredients of a specific dosage form—the capsule.

The Applicant has found that several practical problems are encountered when encapsulation of SAMe or its derivatives is attempted. Encapsulation of SAMe is not as easy as theoretised. The first problem of course is the hygroscopic nature and low pH of SAMe, which does not permit easy encapsulation since the initial high water content of the gelatin shell has an adverse effect on the compound. The second problem is that if the tablet is enteric coated, the coating has to be optimized for the desired availability of SAMe at the target site i.e anterior part of the intestine.

It is on account of these problems that the encapsulated dosage form of SAMe salts are not available in the market. The prior art does not identify these problems nor suggest any solutions to overcome the same. Beyond the development of a simulated capsule like medicament, several factors and considerations must be met to commercially produce a capsule which is storage stable and acceptable to the consumers.

To overcome and provide a solution to the problems in the prior art, the Applicant has conducted a detailed investigation and has developed a pharmaceutical formulation containing SAMe as the active ingredient suitable for encapsulation and a method for producing the said soft gelatin capsules.

In fact, people in the art have not envisaged coating SAMe with soft gelatin film for the reason that because such encapsulation would cause deterioration of SAMe. However, as opposed to that, the Applicant tried the encapsulation and to their surprise found that such encapsulation really achieved the advantages of enhancing the shelf life of SAMe and at the same time achieving 95% protection from degradation.

OBJECTS OF THE INVENTION

The main object of the invention is to provide a soft gelatin capsule encapsulating SAMe as the active ingredient.

Another object is to provide a method for the encapsulation of SAMe.

Yet another object is to provide a method for producing the soft gelatin capsules of the invention.

SUMMARY OF THE INVENTION

In accordance with the above and other objectives, the invention provides a soft gelatin capsule containing S-adenosylmethionine or its stable salts as active ingredients.

DETAILED DESCRIPTION OF THE INVENTION

Accordingly, after lengthy investigations and variations of materials and quantity ratios, the Applicant has developed a novel soft gelatin capsule containing SAME or its salts as active ingredients.

The invention provides a novel soft gelatin capsule comprising a fill material consisting essentially of S-adenosylmethionine (SAMe) salt disposed within an enteric coated soft gelatin film.

The fill material comprises a core of SAMe salt coated with lipophilic material, which is further provided an oily matrix, antioxidants and preservatives.

To counter and avoid the hygroscopicity and low pH problems of SAMe, the Applicant has chosen some of the more stable derivatives of SAMe, i.e. S-adenosylmethionine disulphate and monosulphate tosylate salts. These salts can be prepared by the synthetic route and are biocompatible. The method for preparation of these compounds is also easy.

The soft gelatin capsule of the invention essentially comprises SAMe or its salts as active ingredients, disposed within an enteric coated soft gelatin capsule.

A very essential aspect of the invention resides in the selection of the appropriate filling materials in quantity and ratios that ensure that SAMe is provided in an acceptable dosage form with greater bioavailability. Accordingly, the invention provides soft gelatin capsules of excellent stability and durability which are produced from ingredients, some of which are known, but have never before been combined in this specified form.

Preparation of Fill Material

As a first step, SAMe-disulphate monotosylate salt or monosulphate tosylate salt is coated or insulated with a lipophilic material. Typical examples of such material are stearic acid, carnuaba wax, beeswax, polyoxyethylene sorbitan monooleate, etc. Hydrogenated vegetable oils such as sterotex can also be used for the coating. In the alternative, fatty acid compounds such as cetyl alcohol, glyceryl monostearate, cetostearyl alcohol and glyceryl behanate can be used. These materials may optionally be diluted with dichloromethane or isopropylalcohol.

The substance selected for coating of SAMe-salt is one which is a non-irritant and non-toxic to the human body. Further, the compounds selected for coating are hydrophobic in nature. This coating or insulation protects SAMe salts from any direct exposure to moisture (from gelatin shell or environment) and preserves the integrity of the drug. The amount of SAMe salts in the capsule ranges from 425 mg to 440 mg depending on the assay potency, moisture content and overage.

The amount of the lipophilic material employed for coating SAMe salt may be 15 to 20% w/w. This particular range has been found to be most effective and advantageous, although the art recommends the use of 16% w/w.

The lipophilic material may be diluted with dichloromethane or isopropyl alcohol to achieve best results.

The ratio of the lipophilic material to the drug (SAMe salt) depends on various factors such as the amount of protection sought to be given to the salt and the in vitro dissolution of drug availability. The optimum drug: lipid fill material ratio is 5:1.

Once the salt is coated, it appears as a granular material. "Coating" as used herein means the drug is dispersed in the lipid matrix by conventional methods known in the art. Granules carrying the drug are obtained, which are eventually dried to remove all traces of the diluents, if used. The granules are milled to fine particles of uniform size, preferably 60 mesh to 250 microns.

The granules are suspended in an oily matrix composed of oils selected from soya oil, arachis oil, wheat germ oil, corn oil and rice bran oil.

The oils selected for the oily matrix should be inert, non-toxic, biocompatible, easy to handle, easily available and inexpensive. The oil chosen should also provide appropriate consistency to the lipid fill material and stability in the final product. The oils recommended herein have been chosen with these criteria in mind.

The oily base acts as a viscosity enhancer. The granules in the oily matrix form a lipoid substance. If the viscosity is too high, the fill will face problem of smooth material transfer into the cavity of the capsule. If the viscosity is too thin, there will be loss of fill material due to continuous drip. The viscocity of the lipoid filler material may be adjusted so that it cannot be readily removed from the capsule with syringe at room temperature. This feature helps to protect against possible intravenous abuse of the drug and product tampering.

The amount of oil used is approximately 50–55% w/w of the total fill material used, although use of 53% gives best results.

Antioxidants such as ascorbic acid, may also be added to the blend to further protect the salt from degradation. Butylated hydroxy toulene NDGA and butylated hydroxy anisole may optionally be used as anti-oxidants. The amount of anti-oxidants in the blend may vary depending on the formulation, but the optimum amount may be 0.1% w/w. Additional materials such as preservatives, like paraben may also be added to the fill such material. The fill material thus prepared is a soft viscous mass in a lipoid matrix, which is non-aqueous.

Preparation of Soft Gelatin Capsule

The method of preparing a soft gelatin capsule comprising SAMe, comprises the steps of:

a. coating SAMe salt with a lipophilic material to obtain granules, b. coating the granules obtained in step (a) with an oily matrix, antioxidants and preservatives to form a lipid suspension, c. disposing the lipid suspension within a soft gelatin film, and d. providing the soft gelatin film with an enteric coating to obtain an enteric coated soft gelatin capsule.

The SAMe-salt encapsulated form according to the invention includes SAMe-salt formulation disposed within an enteric coated soft gelatin film. Since the capsule fill consists of lipid suspension, the drug delivery vehicle is a one piece soft gelatin capsule, which is sealed along the seamline. The soft single-piece capsule is preferred as compared to the conventional two-piece capsule, since the soft single-piece capsule does not require additional sealing of the capsule halves as required for the 2-piece capsule. The soft single-piece capsule is also less prone to product tampering and contamination.

The soft gelatin capsule should be immediately covered, protected from the environment and water. The Applicant tried many methods such as encapsulating with hard two piece capsule but failed in their attempts. However, after much trial, the Applicant thought of encapsulating SAMe in the soft gelatin capsule and have been able to achieve this. Once done, there is a guarantee that SAMe will not degrade or be exposed to moisture or other adverse conditions.

It is not easy to develop and produce soft gelatin capsules, under the state of art as such capsules are surrounded by several economic and technological problems. The problems are encountered especially when production of these capsules on commercial scale is attempted. The process technology for manufacture of soft capsules on a large scale are complex. Some processes impose the burden of disposal of net wastes. The invention uses cheap and commonly available materials and does not pose any problem of disposal of the waste.

However, the soft gelatin capsules of the invention are easy to manufacture and can be produced without great expenditure on equipments and production facility.

During the formation of the gelatin capsules, capsule wall material (film) and the fill material are fed into the equipment. The coating or wall material or film, and the fill material are led via tubular jets and thus, seamless soft gelatin capsule of appropriate shape and size are formed.

In developing the soft gelatin capsule of SAMe, it must be recognized that the capsule comprises of the formulation as well as the gelatin film used to encapsulate the formulation. As such, not only is the filled SAMe formulation which is critical to produce the desired bioavailability characteristics but the gelatin film is also critical as it must be compatible with SAMe formulation. One skilled in the art would be aware of the potential fill-shell interactions which could result in both physical and chemical capsule instability. Accordingly, the gelatin film or capsule wall materials utilized to form the capsule for the SAMe dosage form is also critical to the present invention.

For formation of the wall of the soft gelatin capsule, one of the main ingredients of the wall of the capsule is gelatin which is used in an amount of 40% to 60% w/w. Usually gelatin and glycerine are present in different ratios ranging from 1:1 to 1:0.4 depending on the hardness desired for the capsule.

A plasticizer such as PEG 400, or a non-crystallizing solution of sorbitol may be used. If sorbitol is used alone as plasticizer, the amount may be 10 to 20%. If used in combination with other plasticizers, or if any other plasticizers are opted for, the amount may be 8 % to 10% w/w.

Softening agents selected from glycerol, glycerine, triacetin, sorbitol, sorbitan anhydrides and mannitol in the range of 10% to 15% are advantageously added to soften the wall of the capsule. Furthermore, other non-traditional ingredients may be used to plasticize the gelatin such as polyethylene glycol 200 (PEG 200). The amount of the plasticizer used does not exceed 25 to 30%.

The capsule wall or wall of the film may also include other suitable additives such as preservatives and/or coloring agents which commonly utilized to impart a specific characteristic such as color or look to the capsule. As is known, certain colours are specific for specific markets. A color like iron oxide yellow is recommended for the gelatin capsule of the invention. Color may be imparted to the gelatin shell using appropriate dyes. The amount of the colour material may be in the range of 0.25% to 0.5% w/w.

Pharmaceutically acceptable preservatives which may also be included in capsule wall include, for example, methyl and propyl parabens. The amount of the preservatives added may be in the neighbourhood of 0.1 w/w to 0.2% w/w. The preservatives added also act as anti-microbial agents.

Opacifiers, such as titanium dioxide and/or iron oxides; may also be employed to render the capsule opaque. The opacifiers may be present in an amount of 0.2 to 0.5% w/w.

In soft gelatin capsules the gelatin ribbon (from proper gelatin paste formulation) is wrapped around pre-cooled drum which subsequently encases the liquid fill material through sealing along seamline and arrested in appropriate die rolls. Generally, in soft gel capsules formulation, the fill material is non-aqueous and either lipid form or homogenous suspension or emulsion form of the lipoid system. So, there is interaction between fill material and shell. In the present case, the fill material is totally lipid matrix, so interaction is absolutely not possible with the shell.

The thickness of the gelatin capsule may vary depending on the type of the formulation and medicament conditions. However, for the capsule of the present invention, thickness of 1.1 mm is preferred, although the thickness may be in the range of 0.9 mm to 1.1 mm.

The capsule after preparation are dried at 15% RH for a period of 48 hrs at 20 to 25° C. Subsequently the capsule is provided with an enteric coating of methylacrylic acid copolymer.

Pharmaceutical dosage forms are often provided with a coating primarily to protect the acid-sensitive drug from the stomach environment, as it is likely to cause irritation. These coatings are referred as 'enteric coatings'. The coating is however, soluble in the alkaline environment of the intestine, in which the drug in question, i.e. SAMe is sought to be released. The enteric coating also serves a variety of other purposes such as rendering the dosage more palatable, improving appearance, extended release of drug, protection against moisture etc.

The enteric coating is pH dependent. Enteric coating polymer of acrylic acid co-polymer origin (Eudragit L100 55) or cellulosic polymer (HPMCP-55). The enteric coating starts dissolving on and from 5.5 (anterior part of intestine). So after ingestion of capsule for at least 2 hours, the enteric coating will remain intact. Coating is applied through spray coating device in auto-coater. Enteric coating thickness will be 250–350 microns.

The thickness of the enteric coating has been optimised considering food effects, transit time, gastric environment, etc. The enteric coating material is prepared using conventional methods such as reported in U.S. Pat. No. 4,287,221, which is incorporated herein by reference.

The enteric coating may comprise materials such as hydroxypropylmethyl cellulose phthalate (HPMCP), hydroxypropylmethyl cellulose succinate (HPMCS) and carboxymethyl cellulose (CMEC), methylacrylic acid copolymer etc. The Applicant unexpectedly found that when hydroxypropylmethyl cellulose phthalate (HPMCP) and methylacrylic acid copolymer are used for enteric coating, the bioavailability of soft gelatin capsules is increased.

More specifically, the material of the enteric coating and the thickness of the soft gelatin capsules of the invention are designed to keep the capsule intact for a period of at least about 2 hours, after oral administration. The lag time or delay in release of the pharmaceutically active ingredient is 2 hours after contact with gastric juices of the stomach.

In the present invention, applicant found that glycerin could be advantageously used in the dosage form of the invention. The Applicant unexpectedly found that glycerin acts as a humectant when used in the invention. Humectants are hygroscopic ("water-pulling") substances that are incorporated to promote retention of moisture. As such, the amount of gelatin formulations recommended in the invention provide the necessary physical and chemical stability required for use with the fill material. In fact, in the capsule of the present invention, gelatin is used as one of the main ingredients.

The fill material is introduced into the gelatin capsule prepared as above. For the invention, manufacturing conditions must be maintained to ensure that the capsule environment is properly maintained with respect to temperature and relative humidity.

In a preferred embodiment, the soft gelatin capsules of the invention are given oblong shape. The Applicant has found that straight edges or unbowed edges may cause capsules to stick to each other and form 'twins'. Twinning of capsules is also caused if the coating on the capsules is tacky. Twinning often occurs at the time of drying of the capsules. The capsules prepared according to the present invention do not suffer from this problem since period raking is undertaken at the time of capsule manufacture. Also the temperature and moisture conditions are maintained at 15 to 17° C. and RH of 16–20%

For these reasons, the capsules of the invention are thoroughly dried and the coating thereon is such as to avoid the aforesaid problems encountered in the prior art.

Advantages of the Capsule Form of SAMe Over the Tablet Form:

The capsules of the invention are stable and durable and can be used for at least 2 years from the date of its manufacture. Ideally, the capsules should be stored at 8 to 15° C., although they can tolerate temperatures as high as 25° C. The soft gel capsules show better efficacy in terms of enhanced absorption and availability in the body.

SAMe tablets often get softened and discoloured (even sometimes with leaching of active moiety) when exposed at 25° C. and ambient relative humidity conditions. Unlike tablets, SAMe soft gel capsules do not show such degradation when exposed under similar condition.

Tablet dosage form generally incorporates the active moiety in solid matrix which may not be favourable condition for better absorption and availability of the active moiety (SAMe here) in the body.

In the present invention, SAMe is formulated in liquefied lipid matrix through which absorption and availability of the active moiety (SAMe) in body is enhanced. SAMe being hygroscopic and vulnerable towards moisture atack, the technique of wax encapsulation followed by dispersion in lipid matrix (adopted in this invention) confer better stability. Organoleptically, SAMe in soft gel delivery system looks more elegant and convenient over the tablet dosage form.

Below are examples illustrating preparation of soft gelatin capsules of SAMe made in accordance with the teachings of the present invention. The examples presented below are intended to illustrate particular embodiments of the invention and are not intended to limit the scope of the specification, including the claims, in any way.

EXAMPLE 1

For every 100 gm of S-Adenosylmethionine, 20 gm of Stearic acid is to be taken. The Stearic acid is melted to a temperature of about 50–55° C. The melted wax is diluted using dichloromethane.

The solution obtained thus is used to make the dispersion of the drug in the lipid matrix using a suitable mixer like a planetary mixer. The drug embedded granules thus obtained are dried under vacuum at a temperature not exceeding 25° C. to remove all traces of Dichloromethane.

The above granules are milled using a suitable mill and passed through a 60# (ASTM) sieve and a blend is prepared using Soya oil and other viscosity enhancing oily bases. Anti-oxidants, like Ascorbic acid are added to further protect SAMe and Anhydrous Dicalcium Phosphate is added as an additional diluent to the blend.

Lipid system antioxidants like butylated Hydroxy toluene and butylated Hydroxy anisole are added to the oil.

A blend weight of about 1100 mg is optimized to deliver a dose of 200 mg of S-Adenosylmethionine.

The blend is filled into soft gelatin capsule. The gelatin paste consists of plasticisers Glycerine (20% w/w) and Sorbitol (10% w/w). Methylparaben (0.2% w/w) and Propylparaben (0.02% w/w) are added as preservatives. A colour like iron oxide yellow might be added. Thickness of the gelatin film during encapsulation is kept at around 1.1 mm. The capsules are dried at 15% RH for a period of 48 hours at a temperature 20–25° C. Further, the soft gel capsules show better efficacy in terms of enhanced absorption and availability in the body, as compared to the tablet form of SAMe.

EXAMPLE 2

Scale Up for Process Optimization and Machinability Trial

For every 100 gms of S-Adenosylmethionine, 20 gm of Stearic acid is to be taken. The Stearic acid is melted to a temperature of about 50–55° C. and suitably diluted using isopropyl alcohol.

The above solution is added to the drug powder and dispersed using a suitable mixer like a planetary mixer. The drug embedded granules are dried by application of vacuum in the mixer at 760 nm Hg for about 2 hours at slow mixing.

The above granules are milled using a suitable mill and passed through a 60# (ASTM) sieve and a blend is prepared as described in our patent application.

The scale up batches up to 25 kgs have been prepared and after machine trials, it was decided to improve the fluidity of the blend. Hence the blend composition was diluted further and optimized so that 1280 mg of blend delivered a dose of 200 mg of S-Adenosylmethionine instead of 1100 mg reported The optimized composition contained S-Adenosylmethionine 200 mg (with appropriate overages), Stearic acid 84.77 mg, Gel Oil 125 mg, Dicalcium phosphate 75.0 mg, Ascorbic acid 1.1 mg, Citric acid anhydrous 1.1 mg, Methylparaben 2.2 mg, Propylparaben 0.22 mg, Butylated hydroxy anisole 1.1 mg, Butylated hydroxy toluene 1.1 mg, Soyabean oil q.s. 1280 mg.

EXAMPLE 3

The capsules are enteric coated using methacrylic acid copolymer (Eudragit L 100 55). A 8% w/w solution in IPA: Dichloromethane (50:50) is used. Plasticiser like PEG 400 or Triethyl citrate (15% w/w of Polymer) is added to the coating solution. Talc, titanium dioxide and suitable colorants are added to the coating solution.

A weight gain of about 3% w/w of capsule is given to the capsules to ensure desired property.

The Capsules Obtained Were Tested for the Following Test Parameters

| Test Parameters | Results | Specifications |
|---|---|---|
| Description | Yellow coloured enteric coated soft gelatin capsule | Yellow coloured enteric coated soft gelatin capsule |
| Identification by HPLC | Passes | The retention time of sample matches with that of the standard |
| Assay by HPLC: Each enteric coated capsules contain S-Adenosylmethionine ($C_{15}H_{22}N_4O_5S$) % w/w | 95.6 | 90.0–110.0 |
| mg/capsule (based on theoretical net fill weight of 1100 mg) | 191.21 | 180–220.0 mg |
| Drug Release in Acid stage (0.1 N HCl) (% label Claim) | Less than 2.0 | NMT 10% of drug released after 2 hours |
| Dissolution in Buffer stage- pH 7.2 (% Label Claim) | 88.86 | NLT 75% of drug dissolved in one hour. |

NMT = not more than
NLT = not less than

The expression 'meets specification' or 'meets spec' in the Tables means if the soft gel capsules (finished dosage form under consideration) gets deshaped, discoloured, show any leakage or any appearance abnormality—then it does not meet the specification.

The test results of the SAMe blend prepared as per the above invention and the enteric coated soft gelatin capsules prepared with the blend beet the stability requirements as per standard specifications.

3 months stability data at 8° C.–15° C. and 25° C./60% RH for SAMe blend as well as SAMe enteric coated capsules are attached (refer Table 1).

Recommended storage condition: To be stored at controlled room temperature (8–15° C.) from date of manufacture till expiry.

We have carried out scale up studies for establishing the feasibility of the process and machinability trial for preparation of the blend and subsequent encapsulation into a soft gelatin capsule. To avoid problems of extremely viscid consistency and flow behaviour for filling into soft gelatin capsules through automatic high speed machines and to ensure that the residual solvents (analysed by Head Space Gas Chromatography) are kept within the devised level, the formulation and process was optimized further as illustrated below.

Stability studies on 3 batches have been carried out as per the results attached (refer Tables 2 and 3). Instead of Dichloromethane, Isopropyl alcohol has been used in the blend preparation and organic volatile impurities have been studied to confirm its presence in the blend at a very minimal level.

Nutritional fact analysis data was generated since the product is used as a dietary supplement or a nutritional product (refer Table 4)

Analysis of an Optimized Batch of Capsule

| Test Parameters | Results | Specifications |
|---|---|---|
| Description | Enteric coated soft gelatin capsule | Enteric coated soft gelatin capsule |
| Identification by HPLC | Passes | The retention time of sample matches with that of the standard |
| Assay by HPLC: Each enteric coated capsules contain S-Adenosylmethionine ($C_{15}H_{33}N_dO_1S$) % w/w | 105.62 | 95.0–115.0 |
| mg/capsule (based on theoretical net fill weight of 1280 mg) | 211.24 | 190–230.0 |
| Drug Release in Acid stage (0.1 N HCl) (% label Claim) | Less than 2.0 | NMT 10% of drug released after 2 hours |
| Dissolution in Buffer stage- pH 7.2 (% Label Claim) | 85.20 | NLT 75% of drug dissolved in one hour. |

The final product (enteric coated capsules) is to be packed in hermetically sealed glass bottles or cold forming blister (Alu Alu) pack) because these packing method provide the best protection towards moisture ingress and hence would help in retaining maximum potency.

ADVANTAGES OF THE INVENTION

1) The present invention includes an enteric coated soft gelatin capsule of S-Adenosylmethionine as disulfate tosylate salt.

2) The process methodology of the present invention leads successful encapsulation of a hygroscopic material like S-Adenosylmethionine into a soft gelatin capsule and subsequent enteric coating of the same using appropriate enteric coating polymers like Methacrylic acid co-polymer or Hydroxypropyl methylcellulose Pthalate which allows the drug (S-Adenosylmethionine) to be available at duodenum.

3) Soft gelatin capsule of S-Adenosylmethionine is developed through the present invention as superior, dosage forms over the existing tablet dosage form.

4) Enteric coated soft gelatin capsule containing S-Adenosylmethionine is superior choice over enteric coated tablets of S-Adenosylmethionine.

5) The soft gelatin dosage form of S-Adenosylmethionine is unique delivery system comprising of active drug S-Adenosylmethionine incorporated in lipid matrix system.

6) We claim above dosage forms (soft gel) as unique because no such dosage form of S-Adenosylmethionine is available in the market.

7) The superiority of enteric coated soft gelatin capsule is focused on ease of handling, product elegance, stability and better absorption.

8) The enteric coated soft gelatin dosage form (capsule) is odourless, tasteless, easy to swallow.

9) We have incorporated lipid coating material, antioxidants, lipid vehicle in our formulation design which are non-toxic, non-irritant in nature.

10) We have taken sufficient care in manufacturing process through low temperature exposure (not exceeding 28–30° C.) and low humidity (not exceeding 20–25% RH) keeping in view of thermal and moisture lability of the active compound (S-Adenosylmethionine).

11) The formulation design and method of manufacturing ensures reproducible and trouble free operations in large scale manufacturing using high speed sophisticated machineries.

12) The present formulation design ensures safety, health and environmental aspects as per stringent regulatory norms of US and other advanced countries.

TABLE 1

STABILITY DATA OF SAME BLEND FOR ENCAPSULATION

| BATCH NO. | | 1 M | | 2 M | | 3 M | |
|---|---|---|---|---|---|---|---|
| 008/Blend | Initial | 8°–15° C. | 25° C./60% RH | 8°–15 ° C. | 25° C./60% RH | 8°–15° C. | 25° C./60% RH |
| Appearance | White to off white, oily viscous suspension | Meets specification | Meets specification | Meets specification | Meets specification | Meets specification | Meets specification |
| Assay (% Label Claim) | 102.89 | 101.28 | 98.64 | 99.82 | 97.59 | 99.01 | 96.81 |
| Related Substance (%) | 3.88 | 3.92 | 4.66 | 4.01 | 4.68 | 3.82 | 5.11 |

STABILITY DATA OF SAME ENTERIC COATED CAPSULES

| BATCH NO. | | 1 M | | 2 M | | 3 M | |
|---|---|---|---|---|---|---|---|
| 008/Capsules | Initial | 8°–15° C. | 25° C./60% RH | 8°–15 ° C. | 25° C./60% RH | 8°–15° C. | 25° C./60% RH |
| Appearance | Yellow enteric coated capsules | Meets specification | Meets specification | Meets specification | Meets specification | Meets specification | Meets specification |
| Assay (% Label Claim) | 95.60 | 95.21 | 94.64 | 94.83 | 93.15 | 93.13 | 92.43 |
| Related Substance (%) | 4.46 | 4.54 | 7.42 | 4.78 | 8.72 | 5.03 | 9.38 |
| Gastro Resistance and Dissolution | Complies | Complies | Complies | Complies | Complies | Complies | Complies |

TABLE 2

STABILITY DATA (3 BATCHES/12 MONTHS) OF SAME BLEND FOR ENCAPSULATION

| | | 1 M | | 2 M | | 3 M | | 6 M | | 12 M |
|---|---|---|---|---|---|---|---|---|---|---|
| Batch Nos | Initial | 8° C. | 25° C./60% RH | 8° C. | 25° C./60% RH | 8° C. | 25° C./60% RH | 8° C. | 25° C./60% RH | 8° C. |
| SGBI-1001 | | | | | | | | | | |
| Appearance | White to off white, oily viscous suspension | Meets specs | Meets specs | Meets specs | Meets specs | Meets specs | Meets specs | Meets specs | Meets specs | Meets specs |
| Assay | 119.30 | 118.52 | 112.70 | 110.85 | 111.66 | 107.80 | 110.35 | 105.82 | 102.37 | 101.80 |
| RS | 2.01 | 2.51 | 4.68 | 3.28 | 4.72 | 4.92 | 4.90 | 5.83 | 8.58 | 7.21 |
| PD-006 | | | | | | | | | | |
| Appearance | White to off white, oily viscous suspension | Meets specs | Meets specs | Meets specs | Meets specs | Meets specs | Meets specs | Meets specs | Meets specs | Meets specs |
| Assay | 112.45 | 110.47 | 99.26 | 107.82 | 97.52 | 104.38 | 95.30 | 100.65 | 92.16 | 95.26 |
| RS | 23.4 | 2.46 | 5.8 | 3.56 | 6.5 | 4.82 | 7.50 | 5.67 | 8.26 | 6.58 |
| PD-007 | | | | | | | | | | |
| Appearance | White to off white, oily viscous suspension | Meets specs | Meets specs | Meets specs | Meets specs | Meets specs | Meets specs | Meets specs | Meets specs | Meets specs |
| Assay | 114.65 | 109.83 | 98.27 | 105.63 | 97.65 | 102.83 | 94.5 | 99.50 | 90.65 | 97.86 |
| RS | 2.05 | 2.12 | 5.0 | 3.0 | 6.52 | 3.25 | 8.35 | 5.72 | 9.38 | 6.38 |

TABLE 3

STABILITY DATA (3 BATCHES/12 MONTHS) OF SAME ENTERIC COATED CAPSULES

| Batch Nos | Initial | 1 M | | 2 M | | 3 M | | 6 M | 12 M |
|---|---|---|---|---|---|---|---|---|---|
| | | 8° C. | 25° C./60% RH | 8° C. | 25° C./60% RH | 8° C. | 25° C./60% RH | 8° C. | 8° C. |
| DYS/CAPS/005 | | | | | | | | | |
| Appearance | Enteric coated soft gel capsule | Meets specs | Meets specs | Meets specs | Meets specs | Meets specs | Meets specs | Meets specs | Meets specs |
| Assay | 105.62 | 102.85 | 102.67 | 101.92 | 93.35 | 101.85 | 95.6 | 100.76 | 99.86 |
| RS | 4.38 | 5.10 | 6.78 | 5.29 | 8.34 | 5.38 | 9.26 | 6.72 | 7.35 |
| Gastro Resistance and Dissolution | Complies | Complies | Complies | Complies | Complies | Complies | Complies | Complies | Complies |
| DYS/CAPS/006 | | | | | | | | | |
| Appearance | Enteric coated soft gel capsule | Meets specs | Meets specs | Meets specs | Meets specs | Meets specs | Meets specs | Meets specs | Meets specs |
| Assay | 107.60 | 105.21 | 96.64 | 104.83 | 96.52 | 103.13 | 93.15 | 102.65 | 101.80 |
| RS | 4.46 | 4.54 | 7.42 | 4.78 | 8.72 | 5.03 | 9.38 | 5.48 | 6.35 |
| Gastro Resistance and Dissolution | Complies | Complies | Complies | Complies | Complies | Complies | Complies | Complies | Complies |
| DYS/CAPS/007 | | | | | | | | | |
| Appearance | Enteric coated soft gel capsule | Meets specs | Meets specs | Meets specs | Meets specs | Meets specs | Meets specs | Meets specs | Meets specs |
| Assay | 108.35 | 108.26 | 97.28 | 107.29 | 97.86 | 105.65 | 94.62 | 101.85 | 100.36 |
| RS | 4.82 | 4.65 | 7.28 | 4.98 | 8.56 | 4.89 | 9.85 | 6.58 | 7.01 |
| Gastro Resistance and Dissolution | Complies | Complies | Complies | Complies | Complies | Complies | Complies | Complies | Complies |

TABLE 4

NUTRITIONAL FACT ANALYSIS DATA

| S. No. | Test Parameters | Result | Test Method |
|---|---|---|---|
| 1. | Moisture, % w/w | 3.9 | AOAC $12^{th}$ Edn. 1975, Sec 7.003 |
| 2. | Ash, % w/w | 11.5 | AOAC $12^{th}$ Edn. 1975, Sec, 31.012 |
| 3. | Fat, % w/w | 49.4 | AOAC $12^{th}$ Edn. 1975, Sec, 16.055 |
| 4. | Crude Fibre, % w/w | 0.08 | AOAC $12^{th}$ Edn. 1975, Sec, 7.050 |
| 5. | Protein (N × 6.25), % w/w | 13.4 | AOAC $12^{th}$ Edn. 1975, Sec, 20.054 |
| 60. | Sucrose | NIL | AOAC $12^{th}$ Edn. 1975, Sec, 22.097 |
| 7. | Carbohydrate by difference | 21.7 | — |
| 8. | Calorific Value, Kcal/100 g | 585 | — |
| 9. | Vitamin C, mgm/100 g | 87.3 | AOAC $12^{th}$ Edn. 1975, Sec, 43.031 |
| 10. | Saturated fat % | 8.39 | ILPAC std. Methods for the analysis of oils & fat derivatives. $7^{th}$ revised & enlarged Edn. 1987 |
| 11. | Cholesterol content | Not detected | AOAC 1981, 64, Vol. II, Page 54 |
| 12. | Vitamin A content | NIL | JAOAC 1976, 59, Vol. II, 1113–1130 |
| 13. | Sodium, mg/100 g | 4.7 | AOAC $12^{th}$ Edn. 1975, Sec 33 102 |
| 14. | Calcium, mg/100 g | 2.33 | AOAC $12^{th}$ Edn. 1975, Sec 14.014 |
| 15. | Iron, mg/100 g | 7.1 | AOAC $12^{th}$ Edn. 1975, Sec 2 096 |
| 16. | Dietary Fibre, % w/w | | |
| | a. Insoluble | 0.8 | Enzymatic, Gravinmetric |
| | b Soluble | 2.0 | |
| | c Total | 2.8 | |

What is claimed is:

1. An enteric-coated soft gelatin capsule with fill material comprising a core of S-adenosylmethionine salt selected from the group consisting of a S-adenosylmethionine monosulphate tosylate salt and a S-adenosylmethionine disulphate tosylate salt, said salt being coated with lipophilic material, an oily matrix, antioxidants and preservatives, said fill material being disposed within a soft gelatin film.

2. A capsule as claimed in claim 1, wherein the S-adenosylmethionine salt is present in an amount ranging from 425 mg to 440 mg.

3. A capsule as claimed in claim 1 wherein the lipophilic material coated over the S-adenosylmethionine salt is selected from the group consisting of stearic acid, carnuaba wax, beeswax, polyoxyethylene sorbitan monooleate, cetyl alcohol, glyceryl monostearate, cetostearyl alcohol and glyceryl behanate.

4. A capsule as claimed in claim 1 wherein the lipophilic material is diluted with dichloromethane or isopropyl alcohol.

5. A capsule as claimed in claim 1 wherein the amount of lipophilic material is 15 to 20% of the total fill material.

6. A capsule as claimed in claim 5, wherein the amount of lipophilic material is 16% of the total fill material.

7. A capsule as claimed in claim 1 wherein the ratio of lipophilic material to S-adenosylmethionine salt is 5:1.

8. A capsule as claimed in claim 1 wherein the oil in the oily matrix is selected from the group consisting of soya oil, arachis oil, wheat germ oil, corn oil and rice bran oil and mixtures thereof.

9. A capsule as claimed in claim 1 wherein the amount of oil is 50 to 55% w/w of the total fill materials.

10. A capsule as claimed in claim 9, wherein the amount of oil is 53% w/w of the total fill material.

11. A capsule as claimed in claim 1 wherein the antioxidants are selected from the group consisting of citric acid, ascorbic acid, butylated hydroxytoluene, butylated hydroxyanisole and mixtures thereof.

12. A capsule as claimed in claim 1 wherein the amount of antioxidants is 0.1% w/w of the total fill material.

13. A capsule at claimed in claim 1 wherein the preservatives are selected from the group consisting of methyl paraben, propyl paraben and mixtures thereof.

14. A capsule as claimed in claim 1 wherein the soft gelatin film comprises softening agents, plasticizers, opacifying agents, preservatives and colouring agents.

15. A capsule as claimed in claim 14, wherein the gelatin present in the film is from 40 to 60% w/w.

16. A capsule as claimed in claim 14 wherein the softening agent is selected from the group consisting of glycerol, glycerine, triacetin, sorbitol, sorbitan anhydrides and mannitol.

17. A capsule as claimed in claim 14 wherein the amount of softening agent is 10% to 15% w/w of the gelatin content.

18. A capsule as claimed in claim 14 wherein the plasticizer is selected is polyethylene glycol.

19. A capsule as claimed in claim 14 wherein the amount of plasticizer is about 25 to 30% w/w of the gelatin content.

20. A capsule as claimed in claim 14 wherein the opacifiers is titanium dioxide.

21. A capsule as claimed in claim 14 wherein the opacifier is present in an amount of 0.2 to 0.5% w/w of the gelatin content.

22. A capsule as claimed in claim 14 wherein the colouring agent is iron oxide yellow.

23. A capsule as claimed in claim 14 wherein the amount of colouring agent present is 0.25% w/w of the gelatin content.

24. A capsule as claimed in claim 14 wherein the preservative is methyl paraben or propyl paraben.

25. A capsule as claimed in claim 14 wherein the amount of preservatives is 0.2 to 0.5% w/w of the gelatin content.

26. A capsule as claimed in claim 1 wherein the soft gelatin capsule is enteric coated with a coating agent selected from the group consisting of hydroxypropylmethyl cellulose phthalate (HPMCP), hydroxypropylmethyl cellulose succinate (HPMCS), carboxymethyl cellulose (CMEC) and methylacrylic acid copolymer.

27. A capsule as claimed in claim 1 wherein the thickness of the soft gelatin film ranges from about 0.9 to 1.1 mm.

28. A capsule as claimed in claim 1, wherein the enteric coating sustains a pH of 5.5 to 6.8.

29. A capsule as claimed in claim 1, wherein the enteric coating provides release of the S-adenosylmethionine salt within 2 hours of oral administration.

30. A method of preparing an enteric-coated soft gelatin capsule comprising a core of S-adenosylmethionine salt selected from the group consisting of a S-adenosylmethionine monosulphate tosylate salt and a S-adenosylmethionine disulphate tosylate salt, said method comprising the steps of:
   a. coating the S-adenosylmethionine salt with a lipophilic material to obtain granules,
   b. mixing the granules obtained in step (a) with an oily matrix, antioxidants and preservatives to form a lipid suspension,
   c. disposing the lipid suspension within a soft gelatin film, and
   d. coating the soft gelatin film to obtain an enteric coated soft gelatin capsule.

\* \* \* \* \*